(12) United States Patent
Nahas et al.

(10) Patent No.: US 9,376,351 B2
(45) Date of Patent: Jun. 28, 2016

(54) SIMPLE PROCESS TO PRODUCE AND SEPARATE WATER SOLUBLE AND OIL SOLUBLE ANTIOXIDATIVE FLAVORING COMPOSITIONS FROM LABIATAE HERBS USING GREEN SOLVENTS

(75) Inventors: Roger Nahas, Portage, MI (US);
Elizabeth Barren, Kalamazoo, MI (US);
Gregory S. Reynhout, Kalamazoo, MI (US)

(73) Assignee: KALAMAZOO HOLDINGS, INC., Kalamazoo, MI (US)

( * ) Notice: Subject to any disclaimer, the term of this patent is extended or adjusted under 35 U.S.C. 154(b) by 91 days.

(21) Appl. No.: 13/881,259

(22) PCT Filed: Oct. 25, 2011

(86) PCT No.: PCT/US2011/001808
§ 371 (c)(1),
(2), (4) Date: Apr. 24, 2013

(87) PCT Pub. No.: WO2012/060861
PCT Pub. Date: May 10, 2012

(65) Prior Publication Data
US 2013/0217768 A1    Aug. 22, 2013

Related U.S. Application Data

(60) Provisional application No. 61/455,700, filed on Oct. 25, 2010.

(51) Int. Cl.
| | |
|---|---|
| *C07B 63/00* | (2006.01) |
| *C07C 67/58* | (2006.01) |
| *A23L 1/30* | (2006.01) |
| *A61K 36/53* | (2006.01) |
| *B01D 11/02* | (2006.01) |
| *C07C 51/48* | (2006.01) |

(52) U.S. Cl.
CPC ............... *C07B 63/00* (2013.01); *A23L 1/3002* (2013.01); *A61K 36/53* (2013.01); *B01D 11/0288* (2013.01); *C07C 51/48* (2013.01); *C07C 67/58* (2013.01); *A23V 2002/00* (2013.01); *A61K 2236/39* (2013.01)

(58) Field of Classification Search
USPC ........................................................ 514/533
See application file for complete search history.

(56) References Cited

U.S. PATENT DOCUMENTS

| | | | |
|---|---|---|---|
| 4,354,035 A | 10/1982 | Christ et al. | |
| 6,383,543 B1 * | 5/2002 | Reznik | 426/431 |
| 8,808,769 B2 * | 8/2014 | Chitre et al. | 424/756 |
| 2003/0138537 A1 * | 7/2003 | Bailey et al. | 426/542 |
| 2006/0141072 A1 * | 6/2006 | Arvanitidou et al. | 424/729 |
| 2010/0104730 A1 * | 4/2010 | Mehansho et al. | 426/590 |
| 2010/0151098 A1 * | 6/2010 | Catchpole et al. | 426/425 |

OTHER PUBLICATIONS

Sanchez-Campillo et al. (Food and chemical Toxicology 47(2009) 386-39).*
Frankel, E.N., et al., et al., J. Agric. Food Chem., vol. 44, No. 1, 1996, pp. 131-135.
Search Report for PCT/US2011/001806 of Feb. 25, 2012.
Written Opinion for PCT/US2011/001808.
Nutrafur Espanol SA "Organic rosemary extracts flow-chart" Apr. 27, 2007.

* cited by examiner

*Primary Examiner* — Shirley V Gembeh
(74) *Attorney, Agent, or Firm* — Hueschen and Sage

(57) ABSTRACT

Processes for preparing water soluble and oil soluble antioxidant compositions extracted together from Labiatae herbs in a single extraction using an alcohol and water solvent, followed by a simple, yet effective purification step that allows the separation of the water soluble antioxidative fractions containing mainly rosmarinic acid from antioxidative fractions containing mainly carnosic acid and carnosol, without cumbersome acid/base partitioning steps.

5 Claims, 1 Drawing Sheet

Graphical correlation between mass of solvent removed and pH.
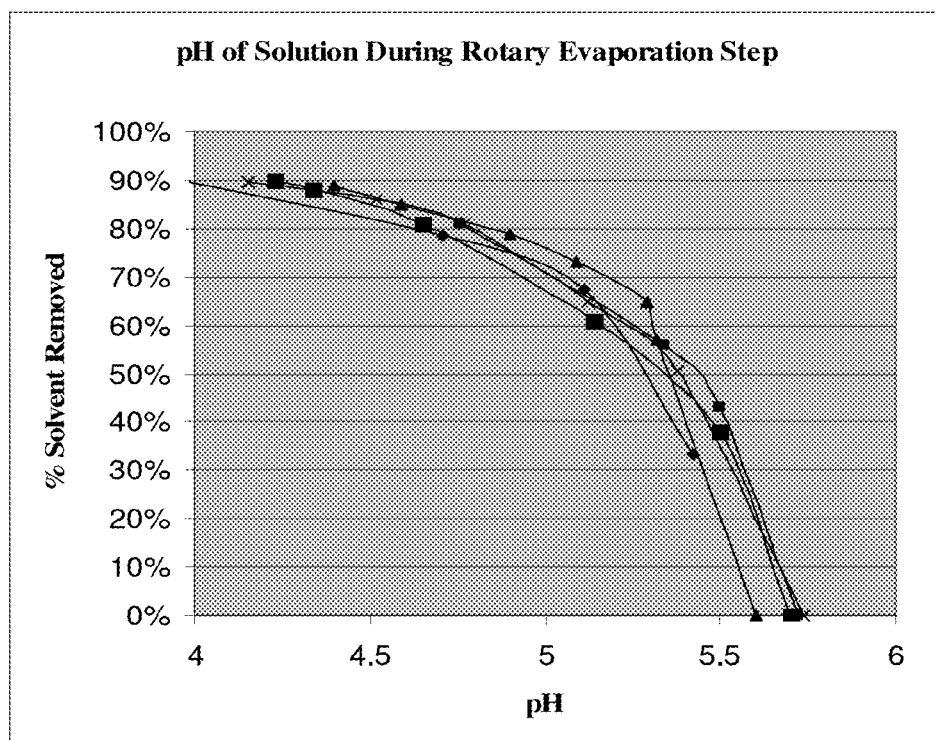

SIMPLE PROCESS TO PRODUCE AND SEPARATE WATER SOLUBLE AND OIL SOLUBLE ANTIOXIDATIVE FLAVORING COMPOSITIONS FROM LABIATAE HERBS USING GREEN SOLVENTS

BACKGROUND OF THE INVENTION

The instant invention relates to processes for preparing water soluble and oil soluble antioxidant compositions extracted together from Labiatae herbs in a single extraction using alcohol and water, followed by a simple, yet effective, purification step that allows the separation of the water soluble antioxidative fractions containing mainly rosmarinic acid from antioxidative fractions containing mainly carnosic acid and carnosol, without cumbersome acid/base partitioning steps.

Substances that serve to protect foods from the deleterious effects of oxidation are commonly added to foods and are called antioxidants or stabilizers. These substances can be naturally or synthetically derived, although consumers generally prefer those materials from natural sources. Rosemary (*Rosmarinus officinalis*) has been used in culinary applications since ancient times and reports on its antioxidant activity date back to the 1950s (Chipault et al., 1956). There are over 250 reports on the potency of dry rosemary, rosemary oleoresin, rosemary extracts and the individual active antioxidant molecules in rosemary (carnosic acid, carnosol, epirosmanol, isorosmanol, methyl-epirosmanol, rosmanol, rosmanidiphenol, rosmarinic acid, rosmariquinone and ursolic acid) in various food systems (Etter, 2004). The most abundant individual antioxidant components in rosemary are the water soluble phenolic acid, rosmarinic acid, and the oil dispersible diterpenoid, carnosic acid.

Due to the high polarity of rosmarinic acid, the most common method for its extraction involves the use of water (according to U.S. Pat. No. 4,354,035), or a highly polar solvent mixture, preferably after removing the fats (also known as defatting or degreasing), de-oiling (removing aromas) or even extracting the carnosic acid and the compounds of similar polarity with a less polar solvent first, before re-extracting with a polar solvent to obtain rosmarinic acid in the water soluble fraction.

On the other hand, carnosic acid, carnosol and other rosemary ingredients of similar polarity are preferably extracted with organic solvents, less polar than water such as methanol, acetone, petroleum ether and hexane, in addition to supercritical $CO_2$ extraction (Chen et al., 1992; Baskan et al., 2007, U.S. Pat. No. 5,256,700).

It is the aim of this invention to provide a method to extract antioxidative flavoring compositions from Labiatae plants using a "green", that is, environmentally friendly, single step extraction, to obtain acceptable yields of both rosmarinic acid (water soluble) and carnosic acid (water soluble at high pH values, and oil dispersible). Subsequently, it is the aim of this invention to solve the problem of separating the water soluble fraction from the carnosic acid fraction, without the need of cumbersome, costly, and difficult to scale, separation and purification processing steps.

We have discovered that Labiatae herbs may be extracted with certain ratios of an ethanol/water mixture to provide both rosmarinic acid and carnosic acid in acceptable yields. The solvent of the post-extraction solution is partially distilled out to a point where, surprisingly, the carnosic acid containing fraction may be separated from the water soluble fraction (containing mainly rosmarinic acid) by simple filtration. The ethanol/water solution is distilled to decrease the pH and to decrease the relative ethanol concentration (and consequently increase the water concentration) to an ethanol level of about 0% to 35%, resulting in a concomitant gradual increase in concentration of both the carnosic acid fraction and water soluble fraction in the solution. At this point in the extraction process, the carnosic acid precipitates from the solution, whereby a carnosic acid fraction is obtained by simple filtration of the solution. The water soluble fraction comprising rosmarinic acid is retained in the solution after filtration of the carnosic acid precipitate.

Thus, the process of the instant invention provides for facile isolation of carnosic acid, which process provides an improvement over the conventional techniques for isolating carnosic acid which may encompass the cumbersome steps of adding acids/bases to transfer the carnosic acid into and out of the aqueous phase, or removing the solvent to complete dryness of the extract and then re-extracting carnosic acid with a non-polar solvent, or solvent/solvent partitioning, or adsorbing carnosic acid onto a resin then selectively extracting it with an appropriate solvent.

BRIEF SUMMARY OF THE INVENTION

The instant invention provides a process to extract and isolate water soluble and oil soluble natural antioxidant flavoring compositions derived from Labiatae herbs, each useful for incorporating, based on their water or oil solubility, into specific foods, beverages, nutritional supplements and cosmetics for the purpose of enhancing the stability of the food, beverage or cosmetic. Other objects, features and advantages of the present invention will become apparent as one reads carefully through the descriptive examples, which are not in any way limiting.

What we therefore believe to be comprised by our invention may be summarized inter alia in the following words:

A process to produce water soluble and oil soluble plant extract fractions comprising, respectively, rosmarinic acid and carnosic acid from Labiatae herbs comprising the following steps:

a) contacting the Labiatae herbs with a solvent comprising about 50%-90% ethanol;

b) filtering to obtain a solution comprising both oil soluble and water soluble plant extract fractions;

c) removing 50%-97% of the solvent from the solution of step b) under vacuum until ethanol levels drop to about 0%-35%, and pH drops simultaneously to about 3-5;

d) separating solid and liquid fractions obtained in step c), and optionally, further purifying the solid fraction comprising carnosic acid and carnosol; and e) removing residual water and ethanol from the liquid fraction to provide a second solid fraction comprising rosmarinic acid, and optionally, further purifying the second solid fraction, such a process wherein the herb is rosemary (*Rosmarinus officinalis*), such a process wherein rosmarinic acid water soluble fractions and/or carnosic acid fractions are further purified by means known in the art, such a process wherein a decolorizing agent is added at step a) to remove undesired color(s), such a process wherein the water soluble and oil soluble plant extract fractions are subjected to a deflavorizing step to remove undesired flavor and/or aroma elements.

The present invention also relates to a water soluble and/or oil soluble plant extract fraction further comprising one or more antioxidant components derived from edible spices, fruits and/or vegetables.

The present invention also relates to a stabilized food, beverage, cosmetic and/or nutritional supplement comprising a water soluble and/or oil soluble plant extract fraction and, optionally, synthetic and/or natural antioxidants of the radical scavenger, metal chelator, secondary antioxidant, quencher, and/or antioxidant regenerator types.

BRIEF DESCRIPTION OF THE FIGURES

FIG. 1. Graphical correlation between mass of solvent removed and pH.

DETAILED DESCRIPTION OF THE INVENTION

We have found that antioxidative, natural flavoring compositions useful for stabilizing foods, cosmetics, beverages and nutritional supplements can be prepared by extracting Labiatae herbs, for example, rosemary (*Rosmarinus officinalis*), with a mixture of ethanol/water wherein the ethanol is present in the aqueous solution in a concentration of about 40%-90% ethanol, including being present in a concentration of 75%-85%, or being present in a concentration of 80% (less ethanol yields higher rosmarinic acid and lower carnosic acid, while more ethanol potentially yields more carnosic acid and less rosmarinic acid). The concentration of ethanol in the extraction medium has a major impact on the levels of other constituents that are extracted, which in turn has an impact on the purity of the antioxidant components as they are separated out of the initial miscella. Higher levels of ethanol will extract higher levels of biomass constituents such as ursolic acid, betulinic acid and oleanolic acid. Higher levels of water will extract higher levels of sugars and other water soluble constituents. These differences can be put to practical use and steps can be incorporated into the overall process to isolate these other biomass constituents in addition to the oil and water soluble antioxidant components, if desired. For example, plant biomass may be left in contact with the extraction solvent for 10 min-24 hours, including for 20 min-5 hours, and including for 30 minutes-3 hours, at a temperature of 20° C.-75° C., 22° C.-55° C., or at a temperature of 25° C.-35° C. Post extraction, 50%-90% of the extraction solvent containing the crude extract is distilled out, for example 70%-95% of the extraction solvent containing the crude extract is distilled out, or 90% of the extraction solvent containing the crude extract is distilled out. The carnosic acid fraction starts precipitating out and can be collected as the pH spontaneously decreases to below 5.5; it is collected when the pH reaches values below 5.0 including when the pH value is below 4.5. The carnosic acid and carnosol fraction is filtered and removed from the solution containing the water soluble fraction (consisting of rosmarinic acid and other water soluble elements from the crude extract), and may be air dried, vacuum dried or heat dried. Alternatively, the carnosic acid fraction may be further purified through processes known in the art, such as recrystalization or trituration, or transferred into a food grade carrier like propylene glycol, and/or lecithin and/or vegetable oil and/or any other carrier recognized in the art.

The water soluble fraction is recovered from the aqueous solution (filtrate) through spray drying, vacuum drying, air drying, or partitioning into an organic solvent (for further purification through acid/base chemistry) or directly into a carrier such as propylene glycol and/or glycerin and/or any other food grade carrier recognized in the art.

The elements in the invention rely on a combination of the following factors occurring in the same process:

- Extraction solvent (ethanol/water) that allows the extraction of both carnosic acid and rosmarinic acid, at acceptable yields (normally the latter is extracted with water or highly polar solvents, and the former is extracted with less polar or non-polar solvents).
- Unexpected ease in feasibility of separating the water soluble fraction from the carnosic acid fraction which allows a different application for each fraction, based on the polarity of the system where each fraction is intended to be used in.
- The precipitation of the carnosic acid fraction that happens after partial removal of solvent due to the coupling of the increase in crude extract concentration, reduction in ethanol levels with the concomitant spontaneous decrease in pH. Therefore, there is no need for a series of cumbersome processing steps typically employed in the art.

EXAMPLES

Example 1

Extraction of Carnosic Acid and Rosmarinic Acid from Rosemary with 20% Ethanol Aqueous Solution Solvent, 0.5 L of 20% ethanol and 80% water, was added to 100 g of dry rosemary leaves, and the mixture was stirred for 30 min at ambient (room) temperature. The solution was filtered and the biomass was separated and discarded. The filtrate was subjected to removal of solvent under reduced pressure (under vacuum) at 60° C. until the pH decrease reached a value of 4.2 and the mass of the solution was simultaneously reduced by 90%, at a concentration of ~20% crude extract in solvent. The solution was filtered, and the solids were dried at 60° C. to yield a solid with a carnosic acid purity of 25% and a carnosic acid yield of 77%. The filtrate was evaporated to dryness under reduced pressure at 70° C. to yield a solid with a rosmarinic acid purity of 9% and a rosmarinic acid yield of 69%. The dry rosemary leaves are preferentially ground prior to extraction.

Example 2

Spontaneous drop in pH leading to ease in isolating the carnosic acid fraction from the solution containing the remaining water soluble fraction.

Several experiments were replicated in order to record the drop in pH of the extraction solution during removal of solvent under reduced pressure, at 60-70° C. FIG. 1 shows a graphical correlation between mass of solvent removed, and a gradual, spontaneous increase in acidity. Eventually, this change in acidity, coupled with an increase in extract concentration and a reduction in ethanol levels allowed vacuum filtration of the carnosic acid fraction from the rest of the crude extract which remained in solution.

Example 3

Purification of Rosmarinic Acid Water Soluble Fractions and/or Carnosic Acid Fractions The carnosic acid fraction from Example 1 is further purified by successively redissolving it in ethyl acetate and repeatedly eliminating the insolubles by filtration. The rosmarinic acid fraction from Example 1 is further purified by decreasing the pH to about 1-2 using phosphoric acid, and isolating rosmarinic acid by extraction with ethyl acetate.

Example 4

Reducing Color Using a Decolorizing Agent

The carnosic acid fraction from Example 1 is further decolorized by redissolving it in a 6% solution of decolorizing carbon, followed by filtration to remove the decolorizing carbon, and removal of excess solvent to obtain a dry carnosic acid fraction with chlorophyll levels lower than 500 ppm. Alternatively, carbon can be added at 2-20% levels to the extraction mixture, with the carbon being removed during the biomass filtration step.

Example 5

Deflavorizing the Antioxidative Carnosic Acid Fraction and/or Water Soluble Rosmarinic Acid Fraction Reducing of the aroma and rosemary flavor levels is performed by dissolving the antioxidant fractions from Example 1 in water, and removing the water by drying under reduced pressure at about 75° C.

Example 6

Formulations Comprising Additional Antioxidant Components Derived from Edible Spices, Fruits and/or Vegetables Antioxidant fractions from Example 1 are formulated in combination with tea extracts in order to provide antioxidant protection in systems with multiple phases of different physico-chemical properties (i.e. water vs. oil), where antioxidants with different physico-chemical properties (i.e. polarity) and functionality (i.e. radical scavenging vs. metal chelating) would be most beneficial.

Example 7

Combination with Other Natural and Synthetic Antioxidants

Italian sausage is formulated with antioxidant fractions from Example 1 in addition to synthetic antioxidants (BHA/BHT, 1:1 ratio), and natural antioxidants (tocopherols) whereas BHA/BHT (200 ppm based on fat content) and tocopherols (300 ppm based on fat content) are dosed as high as the USDA legal limits permit.

REFERENCES

Chipault J H, Mizuno G R, Hawkins J M & Lundberg W O (1956), The Antioxidant Properties of Natural Spices, *Journal of Food Science*, 17, 46-55.

Etter S C (2004), *Rosmarinus Officinalis as an Antioxidant*, *Journal of Herbs, Spices & Medicinal Plants*, 11, 121-159.

Cologne B C, Kottingen, K K (1982), Process for Isolating Rosmarinic Acid from Plants, U.S. Pat. No. 4,354,035, October 12

Aeschbach R, Philippossian (1993), Carnosic Acid Obtention and Uses, U.S. Pat. No. 5,256,700, October 26

The invention claimed is:

1. A process to produce water soluble and oil soluble plant extract fractions comprising, respectively, rosmarinic acid and carnosic acid from Labiatae herbs comprising the following steps:
   a) contacting the Labiatae herbs with a solvent comprising about 50%-90% ethanol for at least 30 minutes;
   b) filtering to obtain a solution comprising both oil soluble and water soluble plant extract fractions;
   c) removing 50%-97% of the solvent from the solution of step b) under vacuum until ethanol levels drop to about 0%-35% and monitoring pH;
   d) discontinuing solvent removal when the pH has been determined to be of a value in a range of about 3-5, and filtering to obtain a solid fraction comprising carnosic acid and carnosol and a liquid fraction;
   e) isolating the solid fraction comprising carnosic acid and carnosol obtained in step d), and optionally, further purifying the solid fraction comprising carnosic acid and carnosol; and
   f) removing residual water and ethanol from the liquid fraction obtained in step d) to provide a second solid fraction comprising rosmarinic acid, and optionally, further purifying the second solid fraction comprising rosmarinic acid.

2. The process of claim 1, wherein the Lab/Wee herb is rosemary (*Rosmarinus officinalis*).

3. The process of claim 1, wherein rosmarinic acid water soluble fractions and/or carnosic acid fractions are further purified by means known in the art.

4. The process of claim 1, wherein a decolorizing agent is added at step a) to remove undesired color(s).

5. The process of claim 1, wherein the water soluble and oil soluble plant extract fractions are subjected to a deflavorizing step to remove undesired flavor and/or aroma elements.

* * * * *